Aug. 9, 1960 D. H. MOREY, JR Plant Pat. 1,964
ROSE PLANT
Filed Oct. 26, 1959
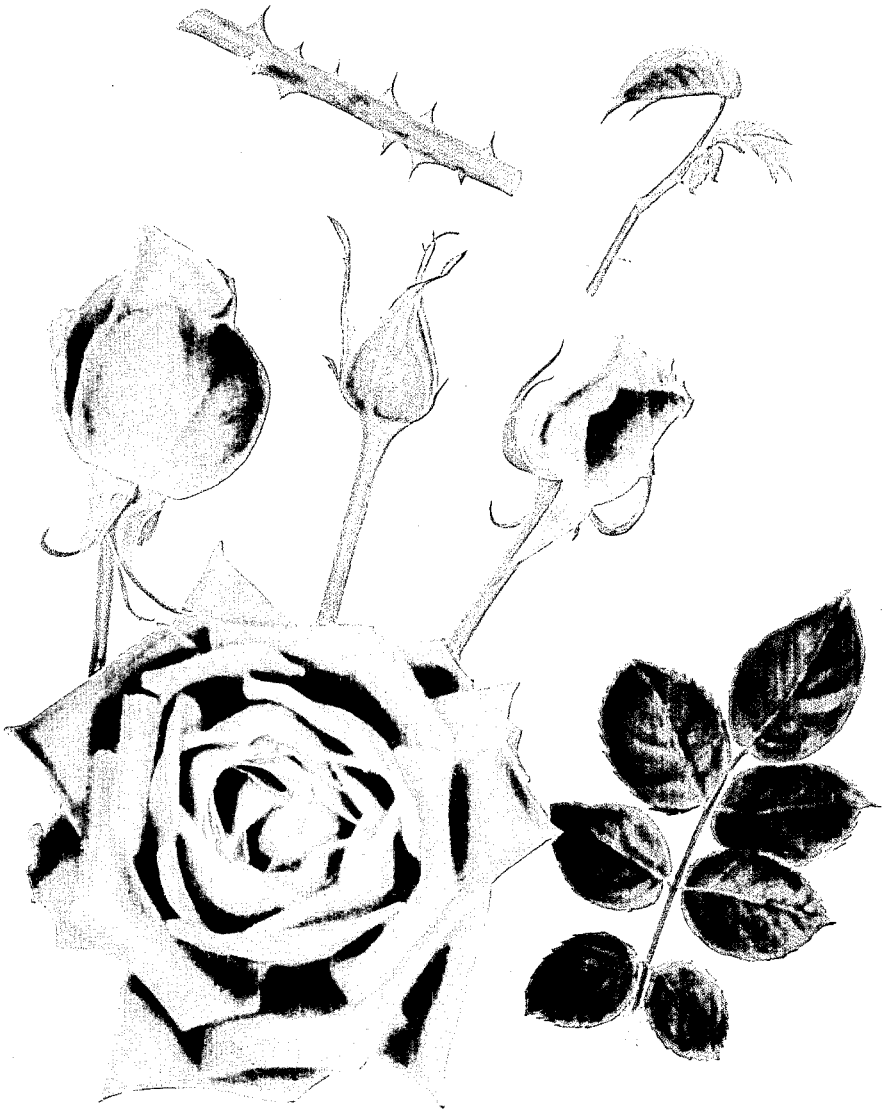
Inventor.
D. H. Morey, Jr
By: Cobb & Cobb
Attorneys.

United States Patent Office

Plant Pat. 1,964
Patented Aug. 9, 1960

1,964

ROSE PLANT

Dennison H. Morey, Jr., Pleasanton, Calif., assignor to Jackson & Perkins Company, Newark, N.Y., a corporation of New York Filed Oct. 26, 1959, Ser. No. 848,880

1 Claim. (Cl. 47—61)

The present invention relates to a new and distinct variety of rose plant of the hybrid tea class, which was originated by me by crossing the variety "Happiness' (Plant Patent No. 911) with the variety "San Fernando" (Plant Patent No. 785).

The primary objective of this breeding was to produce a new rose variety comparable to the parent variety "Happiness," but having a greater flower fragrance, combined with greater flower production. This objective was fully achieved, along with other desirable improvements, as evidenced by the following unique combination of characteristics which are outstanding in the new variety and which distinguish it from its parents, as well as from all other varieties of which I am aware:

(1) A strong and upright habit of plant growth;

(2) Abundant foliage consisting of oval pointed leaflets which clothe the plant very thoroughly;

(3) A habit of breaking many flowers of relatively large size;

(4) A distinctive Carmine, lightly overcast with Scarlet-Red, general color tonality of the flowers; and (5) A very strong and rich flower fragrance.

Asexual reproduction of the new variety by budding, as performed at Pleasanton, California and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—"Happiness."
- *Pollen parent.*—"San Fernando."

Classification:
- *Botanic.*—Hybrid tea.
- *Commercial.*—Hybrid tea.

*Flower*

(Observations made from specimens grown outdoors at Newark, New York in the early morning during the latter part of June.)

Blooming habit: Recurrent—continuous.

Bud:
- *Size.*—Large.
- *Form.*—Ovoid; is not affected by wet or hot weather.
- *Color.*—When sepals first divide—Pomegranate Purple, Plate 12. When petals begin to unfurl—Carmine, Plate 1, lightly overcast with Oxblood Red, Plate 1. When half-blown: inside of petals—Carmine, Plate 1, reverse of petals—Carmine, Plate 1, lightly overcast with Oxblood Red, Plate 1.
- *Sepals.*—Branched ("hood" above bud); curl back when petals begin to unfurl. Color: inside—Light Cress Green, Plate 31; outside—Oil Green, Plate 5.
- *Calyx.*—Color—Oil Green, Plate 5. Shape—funnel. Size—long. Aspect—smooth. Odor when rubbed—none.
- *Peduncle.* — Length — medium. Aspect — smooth. Strength—stiff; heavy. Color—Parrot Green, Plate 6.
- *Opening.*—Opens up well; is not affected by adverse weather conditions.

Bloom:
- *Size.*—Large. Average size when fully expanded—from 4 to 4½ inches.
- *Borne.*—Both singly and several together.
- *Stems.*—Long; strong.
- *Form* (when first open).—Cupped. Permanence—flattens.
- *Petalage.*—Very double (many petals and stamens hidden). Number of petals under normal conditions—from 45 to 50.
- *Color.*—Center of flower—Carmine, Plate 1, lightly overcast with Spectrum Red, Plate 1. Outer petals—Carmine, Plate 1. Base of petals (aiglet)—Lemon Chrome, Plate 4. Inside of petals—Carmine, Plate 1, lightly overcast with Scarlet-Red, Plate 1. Reverse of petals—Spectrum Red, Plate 1. General tonality from a distance—Carmine, Plate 1, lightly overcast with Scarlet-Red, Plate 1.
- *Discoloration.*—General tonality at end of first day—Carmine, Plate 1, lightly overcast with Spectrum Red, Plate 1. Second day—Carmine, Plate 1, lightly overcast with Spectrum Red, Plate 1. Third day—Carmine, Plate 1, lightly overcast with Scarlet-Red, Plate 1.

Petals:
- *Texture.*—Leathery; is not affected by wet or hot weather.
- *Appearance.*—Inside—velvety. Outside—satiny.
- *Form.*—Oval.
- *Arrangement.*—Imbricated (regularly arranged shingle-like).
- *Petaloids in center,*—Few; large.
- *Persistance.*—Drop off cleanly.
- *Frangrance.*—Strong; rich. Nature—tea (average hybrid tea scent).
- *Lasting quality.*—On the plant—long. As cut flower—long.

*Genital organs*

Stamens, anthers: Large; many; regularly arranged around styles. Color—Light Cadmium, Plate 4.

Stamens, filaments (threads): Long. Color—Begonia Rose, Plate 1.

Pollen: Color—Maize Yellow, Plate 4.

Styles: Bunched; uneven length; medium length; thin.

Stigmas: Color—Buff Yellow, Plate 4.

Ovaries: Some protruding from calyx.

Hips: None.

Seeds: None.

Form: Bush.

Growth: Vigorous; upright.

Foliage: Compound of 5 to 7 leaflets.
- *Size.*—Large.
- *Quantity.*—Abundant.
- *Color.*—New foliage: upper side—Yellowish Oil Green, Plate 5, with edges of leaves and serrations overcast with Hay's Russet, Plate 14, under side—Oil Yellow, Plate 5, lightly overcast with Carmine, Plate 1. Old foliage: upper side—Varley's Green, Plate 18; under side—Bice Green, Plate 17.

*Shape.*—Oval pointed.

*Texture.* — Upper side — smooth. Under side—smooth.

*Ribs and veins.*—Prominent.

*Edge.*—Serrated (saw-toothed).

*Serration.*—Single; small.

*Leaf stem.*—Color—Kronberg's Green, Plate 31. Under side—prickly.

*Stipules.*—Short; smooth.

Wood:

*New wood.*—Color—Yellowish Oil Green, Plate 5. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; straight. Color (when young)—Eosine Pink, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novely by the unique combination of a strong and upright habit of plant growth, abundant foliage consisting of oval pointed leaflets which clothe the plant very thoroughly, a habit of producing many flowers of relatively large size, a distinctive Carmine, lightly overcast with Scarlet-Red, general color tonality of the flowers, and a very strong and rich flower fragrance.

No references cited.